United States Patent
Yang et al.

(10) Patent No.: US 7,618,810 B2
(45) Date of Patent: Nov. 17, 2009

(54) METERING STRIP AND METHOD FOR LATERAL FLOW ASSAY DEVICES

(75) Inventors: Kaiyuan Yang, Cumming, GA (US);
Shawn R. Feaster, Duluth, GA (US);
Ning Wei, Roswell, GA (US); Rosann M. Kaylor, Cumming, GA (US);
Chibueze O. Chidebelu-Eze, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/300,650

(22) Filed: Dec. 14, 2005

(65) Prior Publication Data
US 2007/0134810 A1     Jun. 14, 2007

(51) Int. Cl.
| | |
|---|---|
| *G01N 21/00* | (2006.01) |
| *G01N 15/06* | (2006.01) |
| *G01N 33/53* | (2006.01) |
| *G01N 31/00* | (2006.01) |
| *G01N 33/543* | (2006.01) |
| *B01L 3/00* | (2006.01) |
| *B01L 3/02* | (2006.01) |
| *B01L 11/00* | (2006.01) |
| *C12Q 1/00* | (2006.01) |
| *C12M 1/36* | (2006.01) |
| *C12M 1/34* | (2006.01) |
| *C12M 3/00* | (2006.01) |

(52) U.S. Cl. .................. 435/286.5; 422/55; 422/56; 422/57; 422/61; 422/68.1; 422/100; 422/101; 435/4; 435/7.1; 435/286.4; 435/287.1; 435/287.2; 435/287.7; 435/287.9; 435/288.5; 435/288.7; 436/501; 436/518; 436/17; 436/18; 436/825

(58) Field of Classification Search ............. 422/55–57, 422/61, 68.1, 100, 101; 435/4, 7.1, 286.4, 435/287.1, 287.7, 287.9, 288.5, 288.7, 286.5, 435/287.2; 436/501, 518, 17, 18, 825
See application file for complete search history.

(56) References Cited

U.S. PATENT DOCUMENTS 3,700,623 A    10/1972    Keim (Continued)

FOREIGN PATENT DOCUMENTS

EP     0566046 A1    10/1993

(Continued)

OTHER PUBLICATIONS

PCT Search Report—Apr. 5, 2007.

(Continued)

*Primary Examiner*—Bao-Thuy L Nguyen
*Assistant Examiner*—Jacqueline Diramio
(74) *Attorney, Agent, or Firm*—Dority & Manning, P.A.

(57) ABSTRACT

A diagnostic method and associated test kit for detecting an analyte residing in a test sample is provided. The kit includes a housing, and a membrane disposed within the housing having a detection region and a collection region. A blood sample meter is provided having a first end for absorption of a blood sample, a filtering section adjacent to the first end that filters red blood cell components from the blood sample, and a storage section adjacent to the filtering section that receives plasma or serum from the filtering section. An opening in the housing is sized for insertion of the sample meter into the housing such that the storage section of the sample meter is disposed in fluid communication with the collection region of the membrane. The plasma or serum is transferred from the storage section of the sample meter to the collection region of the membrane for subsequent migration to the detection region.

13 Claims, 6 Drawing Sheets

U.S. PATENT DOCUMENTS

| | | |
|---|---|---|
| 3,772,076 A | 11/1973 | Keim |
| 4,168,146 A | 9/1979 | Grubb et al. |
| 4,235,601 A | 11/1980 | Deutsch et al. |
| 4,366,241 A | 12/1982 | Tom et al. |
| 4,426,451 A | 1/1984 | Columbus |
| 4,442,204 A | 4/1984 | Greenquist et al. |
| 4,537,657 A | 8/1985 | Keim |
| 4,614,723 A | 9/1986 | Schmidt et al. |
| 4,742,011 A | 5/1988 | Blake et al. |
| 4,743,560 A | 5/1988 | Campbell et al. |
| 4,810,470 A | 3/1989 | Burkhardt et al. |
| 4,835,099 A | 5/1989 | Mize et al. |
| 4,857,453 A | 8/1989 | Ullman et al. |
| 4,889,816 A | 12/1989 | Davis et al. |
| 4,904,583 A | 2/1990 | Mapes et al. |
| 4,920,045 A | 4/1990 | Okuda et al. |
| 4,954,435 A | 9/1990 | Krauth |
| 4,956,302 A | 9/1990 | Gordon et al. |
| 4,959,324 A | 9/1990 | Ramel et al. |
| 4,963,498 A | 10/1990 | Hillman et al. |
| 4,978,625 A | 12/1990 | Wagner et al. |
| 4,980,298 A | 12/1990 | Blake et al. |
| 4,987,085 A | 1/1991 | Allen et al. |
| 4,999,287 A | 3/1991 | Allen et al. |
| 5,073,340 A | 12/1991 | Covington et al. |
| 5,075,077 A | 12/1991 | Durley, III et al. |
| 5,075,078 A | 12/1991 | Osikowicz et al. |
| 5,120,643 A | 6/1992 | Ching et al. |
| 5,145,784 A | 9/1992 | Cox et al. |
| 5,149,622 A | 9/1992 | Brown et al. |
| 5,185,127 A | 2/1993 | Vonk |
| 5,204,063 A | 4/1993 | Allen |
| 5,208,143 A | 5/1993 | Henderson et al. |
| 5,208,535 A | 5/1993 | Nakayama et al. |
| 5,234,813 A | 8/1993 | McGeehan et al. |
| 5,252,459 A | 10/1993 | Tarcha et al. |
| 5,264,180 A | 11/1993 | Allen et al. |
| 5,275,785 A | 1/1994 | May et al. |
| 5,395,754 A | 3/1995 | Lambotte et al. |
| 5,416,000 A | 5/1995 | Allen et al. |
| 5,423,989 A | 6/1995 | Allen et al. |
| 5,428,690 A | 6/1995 | Bacus et al. |
| 5,464,741 A | 11/1995 | Hendrix |
| 5,518,883 A | 5/1996 | Soini |
| 5,573,909 A | 11/1996 | Singer et al. |
| 5,573,919 A | 11/1996 | Kearns et al. |
| 5,585,279 A | 12/1996 | Davidson |
| 5,589,399 A | 12/1996 | Allen et al. |
| 5,591,581 A | 1/1997 | Massey et al. |
| 5,591,645 A | 1/1997 | Rosenstein |
| 5,602,040 A | 2/1997 | May et al. |
| 5,610,077 A | 3/1997 | Davis et al. |
| 5,622,871 A | 4/1997 | May et al. |
| 5,624,537 A | 4/1997 | Turner et al. |
| 5,637,509 A | 6/1997 | Hemmilä et al. |
| 5,656,503 A | 8/1997 | May et al. |
| 5,670,381 A | 9/1997 | Jou et al. |
| 5,698,406 A | 12/1997 | Cathey et al. |
| 5,714,389 A | 2/1998 | Charlton et al. |
| 5,731,147 A | 3/1998 | Bard et al. |
| 5,736,188 A | 4/1998 | Alcock et al. |
| 5,753,497 A | 5/1998 | Bernstein et al. |
| 5,788,863 A | 8/1998 | Milunic |
| 5,798,272 A | 8/1998 | Allen et al. |
| 5,798,273 A | 8/1998 | Shuler et al. |
| 5,922,537 A | 7/1999 | Ewart et al. |
| 5,945,281 A | 8/1999 | Prabhu |
| 5,981,294 A | 11/1999 | Blatt et al. |
| 5,989,924 A | 11/1999 | Root et al. |
| 5,989,926 A | 11/1999 | Badley et al. |
| 5,998,221 A | 12/1999 | Malick et al. |
| 6,004,530 A | 12/1999 | Sagner et al. |
| 6,030,840 A | 2/2000 | Mullinax et al. |
| 6,036,659 A | 3/2000 | Ray et al. |
| 6,057,165 A | 5/2000 | Mansour |
| 6,077,669 A | 6/2000 | Little et al. |
| 6,130,100 A | 10/2000 | Jobling et al. |
| 6,133,048 A | 10/2000 | Penfold et al. |
| 6,140,136 A * | 10/2000 | Lee ............................ 436/518 |
| 6,156,271 A | 12/2000 | May |
| 6,187,269 B1 | 2/2001 | Lancesseru et al. |
| 6,194,220 B1 | 2/2001 | Malick et al. |
| 6,197,598 B1 | 3/2001 | Schrier et al. |
| 6,235,539 B1 * | 5/2001 | Carpenter .................... 436/514 |
| 6,242,268 B1 | 6/2001 | Wieder |
| 6,258,045 B1 | 7/2001 | Ray et al. |
| 6,261,779 B1 | 7/2001 | Barbera-Guillem et al. |
| 6,270,637 B1 | 8/2001 | Crismore et al. |
| 6,274,324 B1 | 8/2001 | Davis et al. |
| 6,274,384 B1 | 8/2001 | Starzl et al. |
| 6,294,391 B1 | 9/2001 | Badley et al. |
| 6,352,862 B1 | 3/2002 | Davis et al. |
| 6,362,011 B1 | 3/2002 | Massey et al. |
| 6,365,417 B1 * | 4/2002 | Fleming et al. .............. 436/514 |
| 6,399,398 B1 | 6/2002 | Cunningham et al. |
| 6,416,642 B1 | 7/2002 | Alajoki et al. |
| 6,436,651 B1 | 8/2002 | Everhart et al. |
| 6,436,722 B1 | 8/2002 | Clark et al. |
| 6,444,423 B1 | 9/2002 | Meade et al. |
| 6,468,741 B1 | 10/2002 | Massey et al. |
| 6,475,805 B1 | 11/2002 | Charm et al. |
| 6,481,453 B1 | 11/2002 | O'Connor et al. |
| 6,524,864 B2 | 2/2003 | Fernandez de Castro |
| 6,582,930 B1 | 6/2003 | Ponomarev et al. |
| 6,585,939 B1 | 7/2003 | Dapprich |
| 6,613,583 B1 | 9/2003 | Richter et al. |
| 6,620,112 B2 | 9/2003 | Klitmose |
| 6,627,459 B1 | 9/2003 | Tung et al. |
| 6,653,149 B1 | 11/2003 | Tung et al. |
| 6,669,908 B2 | 12/2003 | Weyker et al. |
| 6,673,629 B2 * | 1/2004 | Yoshimura et al. ........... 435/7.1 |
| RE38,430 E | 2/2004 | Rosenstein |
| 6,951,631 B1 | 10/2005 | Catt et al. |
| 7,044,919 B1 | 5/2006 | Catt et al. |
| 7,052,831 B2 | 5/2006 | Fletcher et al. |
| 7,083,939 B2 | 8/2006 | Shull et al. |
| 7,189,522 B2 * | 3/2007 | Esfandiari .................... 435/7.1 |
| 7,225,689 B2 * | 6/2007 | Wickstead et al. ........ 73/863.23 |
| 2002/0042149 A1 | 4/2002 | Butlin et al. |
| 2002/0045273 A1 | 4/2002 | Butlin et al. |
| 2003/0032196 A1 | 2/2003 | Zhou |
| 2003/0113528 A1 | 6/2003 | Moya |
| 2003/0118480 A1 | 6/2003 | Kaylor et al. |
| 2003/0119202 A1 | 6/2003 | Kaylor et al. |
| 2003/0119204 A1 | 6/2003 | Wei et al. |
| 2003/0124739 A1 | 7/2003 | Song et al. |
| 2003/0139886 A1 | 7/2003 | Bodzin et al. |
| 2003/0149348 A1 | 8/2003 | Raskas |
| 2004/0043502 A1 | 3/2004 | Song et al. |
| 2004/0043507 A1 | 3/2004 | Song et al. |
| 2004/0043511 A1 | 3/2004 | Song et al. |
| 2004/0082077 A1 | 4/2004 | Hu |
| 2004/0087034 A1 | 5/2004 | Lien |
| 2004/0106190 A1 | 6/2004 | Yang et al. |
| 2004/0121334 A1 | 6/2004 | Wei et al. |
| 2004/0126833 A1 | 7/2004 | Shull et al. |
| 2004/0151632 A1 | 8/2004 | Badley et al. |
| 2004/0161859 A1 | 8/2004 | Guo et al. |
| 2005/0011759 A1 | 1/2005 | Moerman et al. |
| 2005/0029924 A1 | 2/2005 | Okai et al. |
| 2005/0036148 A1 | 2/2005 | Phelan et al. |

| | | | |
|---|---|---|---|
| 2005/0037510 A1 | 2/2005 | Sharrock et al. | |
| 2005/0084982 A1 | 4/2005 | Brauner | |
| 2005/0109951 A1 | 5/2005 | Fish et al. | |
| 2005/0112635 A1 | 5/2005 | Gentle et al. | |
| 2005/0112780 A1 | 5/2005 | Song | |
| 2005/0136500 A1 | 6/2005 | Yang et al. | |
| 2006/0051237 A1* | 3/2006 | Wang et al. | 422/56 |
| 2006/0127924 A1 | 6/2006 | Hellyer et al. | |
| 2006/0246597 A1 | 11/2006 | Feaster et al. | |
| 2006/0246600 A1 | 11/2006 | Yang et al. | |
| 2007/0134811 A1* | 6/2007 | Takeuchi et al. | 436/514 |

FOREIGN PATENT DOCUMENTS

| | | |
|---|---|---|
| EP | 0883159 A2 | 4/1998 |
| GB | 2090659 A | 7/1982 |
| WO | 0017626 | 3/2000 |
| WO | WO 0050891 A1 | 8/2000 |
| WO | 0054024 | 9/2000 |
| WO | WO 0063697 A1 | 10/2000 |
| WO | WO 0078917 A1 | 12/2000 |
| WO | WO 0117797 A1 | 3/2001 |
| WO | WO 0198785 A2 | 12/2001 |
| WO | WO 0198785 A3 | 12/2001 |
| WO | WO 03008971 A2 | 1/2003 |
| WO | WO 03008971 A3 | 1/2003 |
| WO | WO 03025574 A1 | 3/2003 |
| WO | WO 03058246 A1 | 7/2003 |

OTHER PUBLICATIONS

Article—*Flow-Based Microimmunoassay,* Hayes et al., Anal. Chem., vol. 93, No. 24, Dec. 15, 2001, pp. 5896-5902.

Report by David L. Carlberg entitled *High-volume Manufacturing of Lateral Flow Assays,* 3 pages, (2001).

Data Sheet for MF-Millipore™ Filters from Millipore, 5 pages, (2001).

Product Catalogue—MF-Millipore™ Membrane Filters, 6 pages, Feb. 21, 2005, www.millipore.com.

Product Information Sheet—Nitrocellulose in Solution from Wolff Cellulosics, 4 pages, Feb. 21, 2005, www.wolff-cellulosics.de.

English Abstract of DE 10222979 A1, Dec. 11, 2003.

Article: *Solvent-Assisted Microcontact Molding: A Convenient Method for Fabricating Three-Dimentional Structures on Surfaces of Polymers,* Enoch Kim et al., Advanced Materials, vol. 9, No. 8, Jun. 1997, pp. 651-654.

Article: *Inkjet Printed Via-Hole Interconnections and Resistors for All-Polymer Transistor Circuits,* Takeo Kawase et al., Advanced Materials, vol. 13, No. 21, Nov. 2, 2001, pp. 1601-1605.

Takeuchi, et al., U.S. Appl. No. 11/301,631, filed Dec. 13, 2005, Metering Technique for Lateral Flow Assay Devices.

* cited by examiner

REPLACEMENT SHEET

METERING STRIP AND METHOD FOR LATERAL FLOW ASSAY DEVICES

BACKGROUND OF THE INVENTION

Test strips are often used for qualitative and quantitative analysis of blood components. The test strips are sometimes constructed so that the sample application area and the detection area are stacked above one another in a vertical axis. However, this type of construction is associated with a number of problems. For example, when the test strip is inserted into an instrument for measurement, the potentially infectious sample material may contact parts of the optical reader and result in contamination. Thus, spatial separation between the sample application area and detection zone is often desired, i.e., lateral flow strips. Most conventional lateral flow strips are designed for test samples that are readily available in large quantities (e.g., urine). However, when the test sample is blood, the collection of a large sample may cause undue pain to the patient. Thus, one technique that has been utilized to accommodate smaller test sample volumes is to "spot" the sample directly on the membrane surface. Thereafter, a diluent is used to wash away the test sample and carry it to the detection zone. Unfortunately, variations associated with sample transfer and diffusion of the sample to the membrane result in a flow that is largely uncontrolled and uneven before reaching the detection zone. This may have an adverse effect on the accuracy of the device because the amount of analyte and/or label captured across the detection zone is not consistent at the time of measurement.

In addition, various tests on blood samples require separation of the red blood cell components from the sample to obtain plasma or serum that is essentially free of red blood cells. The sample can then be used in various assays without interference from red blood cell components. In this regard, filter arrangements have been proposed for production of serum or plasma from whole blood. For example, U.S. Pat. No. 5,423,989 describes a membrane filtering arrangement with a first coarse membrane coated with a fibrous protein and a second fine membrane for removing red blood cells from a test sample. The blood sample is generally one or several small drops having a volume of from 10 to 100 microliters. The filtering membranes are arranged in a holder above a sample receiving element, and the blood sample is introduced into a well above the holder so that the blood flows through the coarse membrane and fine membrane before being deposited onto the sample receiving element, which may be round, square, rectangular, quadrilateral, or polygonal. The reference describes that the sample receiving element may be used in any convenient manner, including being diluted in an assay medium.

The arrangement according to the '989 patent is relatively complicated in that it calls for support structure for the filtering membranes and sample receiving element, and requires the user to separate the sample element from the structure for further analysis. The sample element may not be a size or configuration for direct use in an assay device, and may need to be further reconfigured (e.g., cut) for operation with the assay device.

As such, a need currently exists for a simple and efficient technique for metering and filtering a low volume blood test sample such that a known volume of blood plasma or serum may be easily transferred to a detection zone of a lateral flow assay device.

SUMMARY OF THE INVENTION

Objects and advantages of the invention will be set forth in part in the following description, or may be obvious from the description, or may be learned through practice of the invention.

In accordance with one embodiment of the present invention, a diagnostic method and test kit for practice of the method are provided for detecting the presence of an analyte within a blood test sample. The kit and associated method of use are particularly well suited for use with relatively small blood samples of generally less than 10 microliters. The test kit includes a lateral flow assay device having a housing and a membrane disposed within the housing, the membrane having a detection region and a collection region. A blood sample meter is provided having a first end for absorption of a blood sample, a filter section adjacent the first end that filters red blood cell components from the blood sample, and a storage section adjacent the filtering section that receives the plasma or serum from the filtering section. An opening in the housing is sized for insertion of the sample meter into the housing such that the storage section of the sample meter is disposed adjacent to the collection region of membrane. The storage section is brought into fluid communication with the collection region of the membrane (by direct contact or through an intermediary member) and the filtered plasma or serum is transferred from the storage section of the sample meter to the collection region of the membrane for subsequent migration to the detection region. A diluent may be supplied to the collection region to facilitate flow of the test sample from the collection region to the detection region of the membrane.

In a particular embodiment, the sample meter includes a separation membrane material attached to a storage membrane with an overlap between the membranes. The separation membrane serves to intake the blood sample and separate out red blood cell components. Filtered plasma or serum is transferred to the storage membrane in the overlap region of the membranes. It should be appreciated that the sample meter is not limited by dimensions or shape. For example the separation membrane may have a length of between about 3 to about 12 mm, and the overlap region between the separation and storage membranes may be between about 1 mm to about 3 mm. The storage membrane may have a length of between about 10 mm to about 40 mm. In a particular embodiment, the sample meter is an elongated member having a width of between about 1 mm to about 5 mm, and a length of between about 25 mm to about 40 mm. The separation membrane may extend to the first end of the sample meter, and the storage membrane may extend to an opposite second end of the sample meter.

To add structural rigidity to the sample meter, it may be desired to attach the filter and storage membranes to a backing strip. This backing strip may be generally transparent so that migration of the blood plasma or serum to the storage section of the meter may be observed through the backing strip material.

The test kit may incorporate an internal source of diluent that is applied so as to flow to the collection region subsequent to insertion of the sample meter into the assay housing. For example, the diluent may be stored in a rupturable container or pouch within the housing. Means may be provided for rupturing or otherwise breaching this container subsequent to insertion of the sample meter into the housing. For example, a push-button mechanism or other manually actuated device may be configured with the assay housing whereby, upon actuation of the mechanism, a point or blade configured on the mechanism pierces the container causing the diluent to flow to the collection region of the membrane. The mechanism may also serve to compress the container so as to force the diluent therefrom towards the direction of the membrane. It should be appreciated that any number of manually actuated devices may be readily configured by those skilled in the art for this purpose, and all such devices are within the scope and spirit of the invention.

In an alternate embodiment, the test kit may include an external diluent source, with the assay housing configured for fluid communication with this external source. For example, the diluent may be supplied in a disposable, squeezable container having a nozzle that communicates with a port on the assay housing. This port may be configured to internally direct the diluent directly to the collection region of the membrane.

In certain applications, it may be desired to present a precisely defined portion of the meter storage section to the membrane collection region by cutting or scoring the meter. In this regard, means may be supplied in the assay housing for cutting or scoring the meter subsequent to insertion of the meter and in conjunction with or before supplying the diluent. Such means may take on various forms. For example, a push-button device or other manually actuated device may be configured with the assay housing with a blade or knife edge that cuts or scores the sample meter upon actuation thereof. This device may be incorporated with the same device used to breach or rupture an internal diluent pouch, as discussed above.

The invention also encompasses any manner of the blood sample meters discussed above as stand-alone products for subsequent use with a compatible assay device.

Additionally, the invention encompasses all variations of methods of use the blood sample meters and associated assay devices, as described above.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
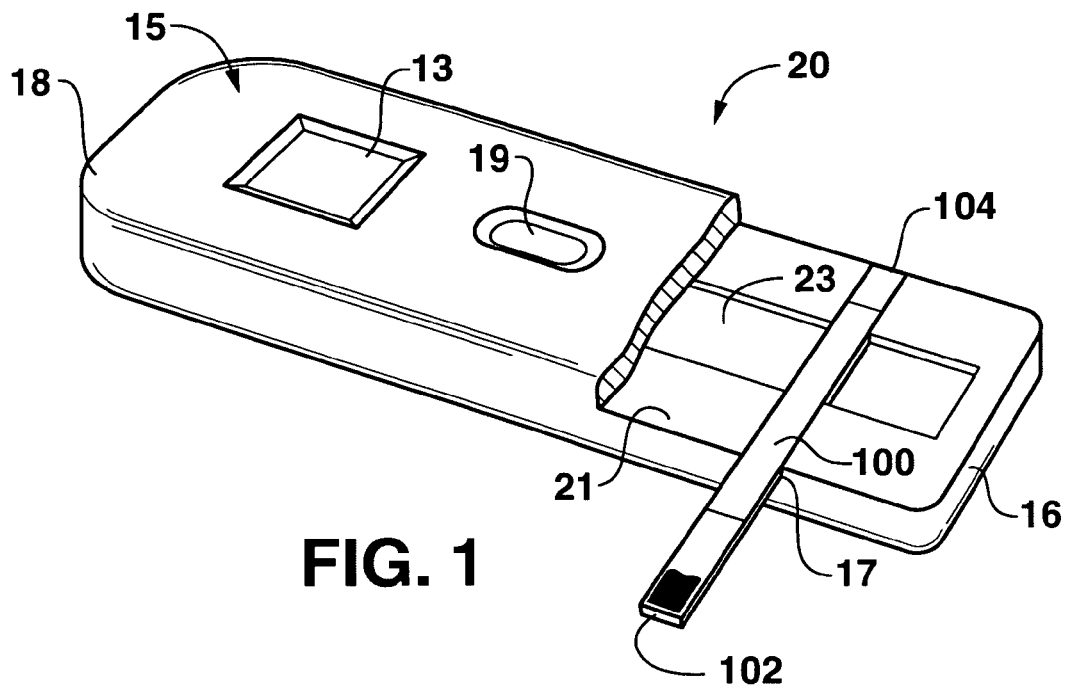
FIG. 1 is a perspective and partial cut-away view of one embodiment of a lateral flow assay device utilizing a sample meter in accordance with aspects of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenyloin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 microglobulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. Nos. 6,436,651 to Everhart, et al. and 4,366,241 to Tom et al.

As used herein, the term "test sample" generally refers to a biological material suspected of containing the analyte. The test sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, food products, and so forth, for the performance of environmental or food production assays. In addition, a solid material suspected of containing the analyte may be used as the test sample. The test sample may be used directly as obtained from the biological source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, lysing, etc. Moreover, it may also be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is directed generally to diagnositc method (and test kit for practice of the method) for detecting the presence of an analyte within a blood test sample. The kit and associated method of use are particularly well suited for use with relatively small blood samples of generally less than 10 microliters. Referring to the figures in general, the test kit includes a lateral flow assay device 20 having a housing 15. The housing may include multiple components, such as an upper member 18 attached to bottom member 16. A sample collection window 19 and detection window 13 may be provided in upper member 18. The particular shape and construction of the housing 15 is not a limiting fearture of the invention.

A membrane 23 is disposed within the housing and includes a detection region 31 and a collection region 30. This membrane 23 is described in greater detail below.

A blood sample meter 100 is provided having a first end 102 for absorption of a blood sample 150 (FIG. 2C), a filter section 106 adjacent the first end 102 that filters red blood cell components from the blood sample, and a storage section 108 adjacent the filtering section 106 that receives the plasma or serum from the filtering section 106. An opening 17 in the housing, for example in a side of the housing 15, is sized for insertion of the sample meter 100 into the housing 15 such that the storage section 108 of the sample meter 100 is disposed adjacent to the collection region 30 of membrane 23. The storage section 108 is brought into fluid communication with the collection region 30 of the membrane 23 (by direct contact or through an intermediary member) and the filtered plasma or serum is transferred from the storage section 108 to the collection region 30 of the membrane 23 for subsequent migration to the detection region 31. A diluent may be supplied to the collection region 30 to facilitate flow of the test sample from the collection region 30 of the membrane 23 to the detection region 31.

The combination of the sample meter 100 and membrane 23 is particularly effective for embodiments in which the blood test sample has a relatively low volume, such as less than about 10 microliters, in some embodiments less than about 5 microliters, and in some embodiments, between about 1 and about 3 microliters. For example, whole blood drops obtained from patients with a lancet from low-pain areas having reduced nerve endings as compared to a fingertip, such as the forearm, thigh, or other alternate sites, may have a volume of less than about 5 microliters. Despite such low volumes, the kit and method of the present invention is effective in separating red blood cell components and providing a filtered test sample of plasma or serum that may be accurately analyzed for the presence of an analyte using lateral flow detection techniques.

In general, the membrane 23 may be made from any of a variety of materials through which the test sample is capable of passing. For example, the membrane 23 may be formed from natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. Particularly desired materials for forming the membrane 23 include polymeric materials, such as nitrocellulose, polyether sulfone, polyethylene, nylon, polyvinylidene fluoride, polyester, and polypropylene. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The size and shape of the membrane 23 may generally vary as is readily recognized by those skilled in the art. For instance, a membrane strip may have a length of from about 10 to about 100 millimeters, in some embodiments from about 20 to about 80 millimeters, and in some embodiments, from about 40 to about 60 millimeters. The width of the membrane strip may also range from about 0.5 to about 20 millimeters, in some embodiments from about 1 to about 15 millimeters, and in some embodiments, from about 2 to about 10 millimeters. Although not required, the thickness of the membrane strip may be small enough to allow transmission-based detection. For example, the membrane strip may have a thickness less than about 500 micrometers, in some embodiments less than about 250 micrometers, and in some embodiments, less than about 150 micrometers.

As stated above, the support 21 carries the membrane 23. For example, the support 21 may be positioned directly adjacent to the membrane 23 as shown in the various figures, or one or more intervening layers may be positioned between the membrane 23 and the support 21. Regardless, the support 21 may generally be formed from any material able to carry the membrane 23. The support 21 may be formed from a material that is transmissive to light, such as transparent or optically diffuse (e.g., transluscent) materials. Also, it is generally desired that the support 21 is liquid-impermeable so that fluid flowing through the membrane 23 does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth.

To provide a sufficient structural backing for the membrane 23, the support 21 is generally selected to have a certain minimum thickness. Likewise, the thickness of the support 21 is typically not so large as to adversely affect its optical properties. Thus, for example, the support 21 may have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers may be obtained from Millipore Corp. of Bedford, Mass. under the name "SHF180UB25."

As is well known the art, the membrane 23 may be cast onto the support 21, wherein the resulting laminate may be die-cut to the desired size and shape. Alternatively, the membrane 23 may simply be laminated to the support 21 with, for example, an adhesive. In some embodiments, a nitrocellulose or nylon membrane is adhered to a Mylar® film. An adhesive is used to bind the membrane to the Mylar® film, such as a pressure-sensitive adhesive. Laminate structures of this type are believed to be commercially available from Millipore Corp. of Bedford, Mass. Still other examples of suitable laminate assay device structures are described in U.S. Pat. No. 5,075,077 to Durley, III, et al., which is incorporated herein in its entirety by reference thereto for all purposes.

The device 20 may also contain an absorbent pad (not shown). For example, the absorbent pad may be positioned adjacent to or near an end 27 of the membrane 23. The absorbent pad generally receives fluid that has migrated through the entire membrane 23. As is well known in the art, the absorbent pad may assist in promoting capillary action and fluid flow through the membrane 23.

The test membrane 23 includes the collection region 30, which is the portion of the membrane disposed to receive the metered portion of the test sample from the sample meter 100. The collection region 30 collects and temporarily stores the test sample before the sample is conducted to a detection region 31, as described in greater detail below.

Figure 2A:
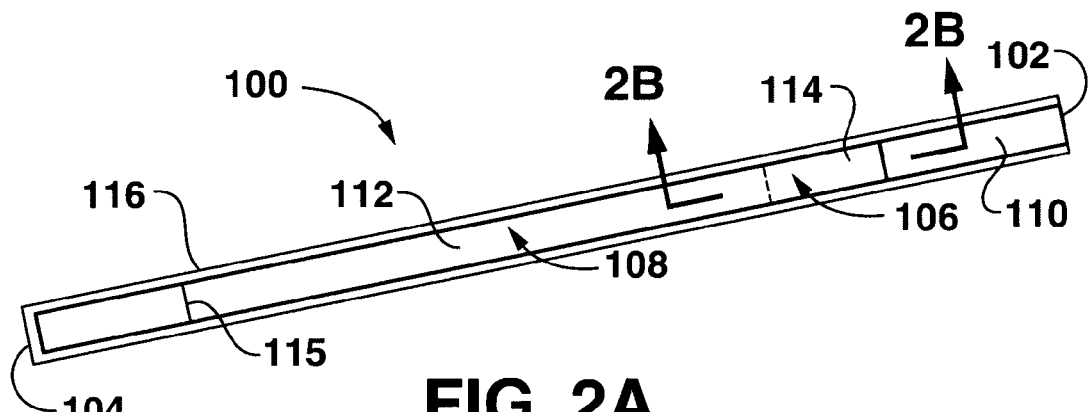
FIG. 2A is a top perspective view of an embodiment of a sample meter.
Figure 2B:
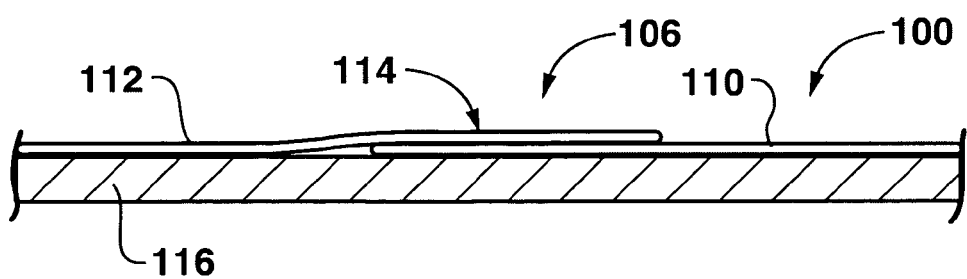
FIG. 2B is a cross-sectional view of the sample meter of FIG. 2.
Figure 2C:
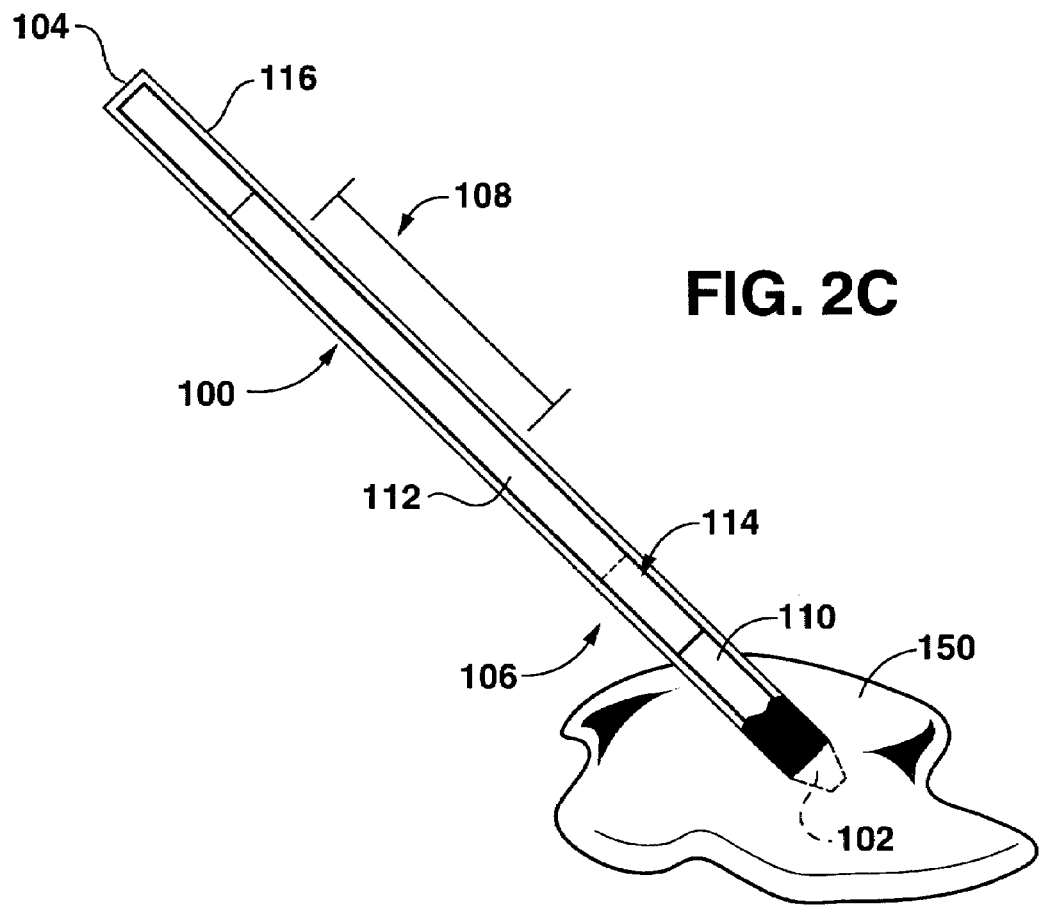
FIG. 2C is a perspective view of the sample meter of FIG. 2A being used to collect a blood sample.

FIGS. 2A through 2C illustrate an embodiment of the sample meter 100 that may be used with an assay device 20 according to the invention. The sample meter 100 may generally take on any desired shape, size, or configuration. In the illustrated embodiment, the sample meter 100 is an elongated strip member having first end 102 and an opposite end 104. The first end 102 is configured for absorption of a blood sample 150, as depicted in FIG. 2C. The meter 100 includes a filter section 106 adjacent to the first end 102 that filters red blood cell components from the blood sample 150. A storage section 108 is adjacent to the filtering section and receives filtered plasma or serum from the filtering section 106.

In particular embodiments, the sample meter 100 includes a separate membrane 110 at the filter section 106. This separation membrane 110 is selected from a known class of materials capable of filtering red blood cell components from fluids, examples of which are provided below. The sample meter 100 includes a storage membrane 112 disposed to receive filtered plasma or serum from the separation membrane 110. For example, in a particular arrangement of the materials, the separation membrane 110 and storage membrane 112 overlap along at least a portion of their length in an overlap region 114 depicted for example in FIG. 2B. In this overlap region 114, filtered plasma or serum is transferred from the separation membrane 110 to the storage membrane 112.

It should be appreciated that the sample meter 100, or its constituent membrane components 110, 112, are not limited by dimensions or shape. For example, the separation membrane 110 may have a length of between about 3 to about 12 mm. The overlap region 114 between the separation and storage membranes may be between about 1 mm to about 3 mm. The storage membrane 112 may have a length of between about 10 mm to about 40 mm. In a particular embodiment, the sample meter 100 has the elongated strip shape illustrated in the figures with a width of between about 1 mm to about 5 mm, and a total length of between about 25 mm to about 40 mm. The separation membrane 110 may extend to the first end 102 of the meter 100, and the storage membrane 112 may extend to the opposite second end 104 of the meter 100.

The storage membrane 112 may comprise any material through which test samples are capable of passing. For example, the storage membrane 112 may be formed from any of the natural, synthetic, or naturally occurring materials identified above as suitable for use as membrane 23. A particularly useful material is a nitrocellulose membrane (Millipore Inc. HF 120 or 75).

The separation membrane 110 may be any suitable material, for example, a hydrophobic material capable of filtering cells (e.g., blood cells) from fluids. Various packings or sieving depth filters may be employed, such as glass fibers, cellulose or glass filters treated with red blood cell capture reagents, glass fiber filters, synthetic fiber filters or a composite material including any combination of the above materials. Glass fiber filters, for instance, are commercially available from Whatman plc of Kent, United Kingdom; Millepore Corp. of Billerica, Mass.; and Pall Corp. of Ann Arbor, Mich. Such glass fiber filters may have a fiber diameter in the range of about 0.05 to about 9 micrometers and a density of about 50 to about 150 g/m$^2$. Other examples of suitable blood separation filters are described in U.S. Pat. No. 5,416,000 to Allen, et al., as well as U.S. Patent Application Publication Nos. 2004/0126833 to Shull, et al. and 2003/0032196 to Zhou, all of which are incorporated herein in their entirety by reference thereto for all purposes. If desired, the blood separation filter may be treated with one or more reagents (e.g., agglutinin), such as described above. In a particular embodiment, a useful separation membrane is vertical blood separation membrane from PALL Inc. identified as "BTS SP 300."

To add structural rigidity and additional functionality to the sample meter 100, it may be desired to attach the separation and storage membranes 110, 112 to a backing strip 116, as particularly illustrated in FIGS. 2A through 2C. Preferably, this backing strip 116 is a generally transparent material so that migration of the blood plasma or serum to the storage section 108 of the meter 100 may be observed through the backing strip material 116.

The sample meters 100 may be made with various processing steps. In a particular embodiment, strips of a material such as Millipore nitrocellulose HF 75 or HF 120 may be laminated onto a transparent card material that serves as the backing strip 116. A separate piece of blood separation material serving as the separation membrane 110 may then be laminated onto the transparent card material with the desired overlap between the storage membrane material. The card with laminated materials may then be processed through a Kinematic slitter from Kinematic Automation, Inc., or other suitable cutting device, to cut the assembled card into strips having a desired width dimension (e.g. 1 mm, 2 mm, or so forth). It should be readily appreciated that economical mass production of the sample meters 100 is possible, and is contemplated within the scope and spirit of the invention.

Figure 3:
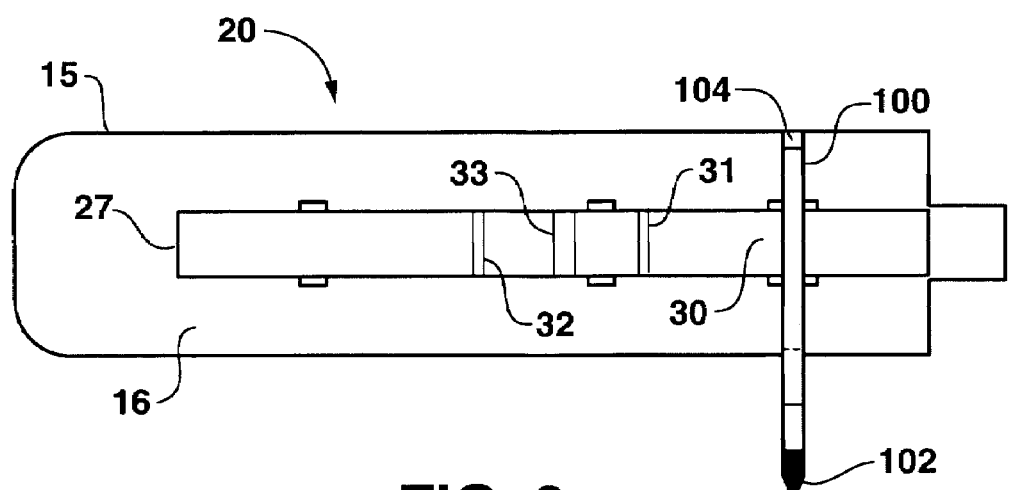
FIG. 3 is a top planar view within an embodiment of a lateral flow assay device utilizing a sample meter.

As mentioned, after the sample meter 100 has been used to collect a suitable sample and separate plasma or serum from the blood sample, as depicted in FIG. 2C, the meter 100 may be inserted into a lateral flow assay device such that the storage section 108 lies adjacent to the membrane 23. This configuration is depicted generally in FIG. 1. In the particular embodiment of FIG. 1, the sample meter 100 is inserted so as to lie beneath the membrane 23. In alternate embodiments, the sample meter 100 may lie above the membrane 23. For example, in the embodiment of FIG. 3, the sample meter 100 is depicted as laying on top of the membrane 23 such that the storage section 108 is in fluid contact with the collection region 30 of the membrane 23.

Any number of configurations may be utilized to bring the storage section 108 of the sample meter into fluid communication with the collection region 30 of the membrane 23. For example, in the embodiment of FIGS. 4A and 4B, a channel 35 is defined completely across the width of the membrane 23 and has a width corresponding essentially to the width of the sample meter 100 so that the user may readily slide the sample meter 100 into the opening 17 in the assay housing 15 (FIG. 1) and be assured that the meter is correctly positioned. In this regard, the end 104 of the sample meter 100 may abut against a side wall of the housing 15 as an indication that the meter 100 has been fully inserted into the housing. The storage section 108 of the meter 100 may be scored, for example at location 115 (FIG. 2A), so as to prevent migration of the plasma or serum to the extreme end 104, and to thus concentrate the plasma or serum at a location adjacent to the collection region 30 of the membrane 23.

Figure 4A:
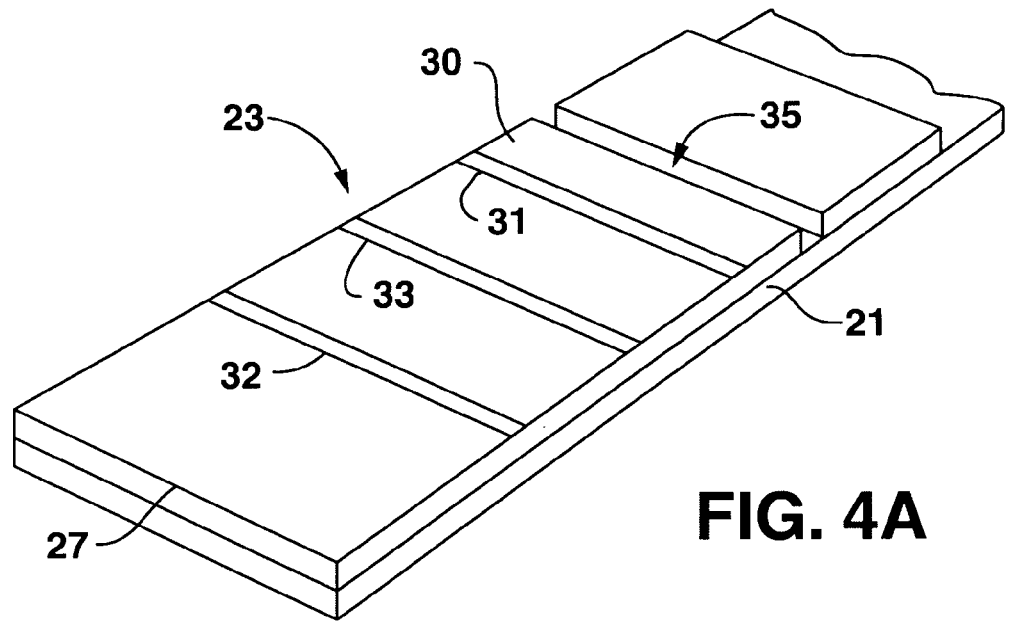
FIG. 4A is a perspective view of an embodiment of a test membrane configured for use with a sample meter within a lateral flow assay device.
Figure 4B:
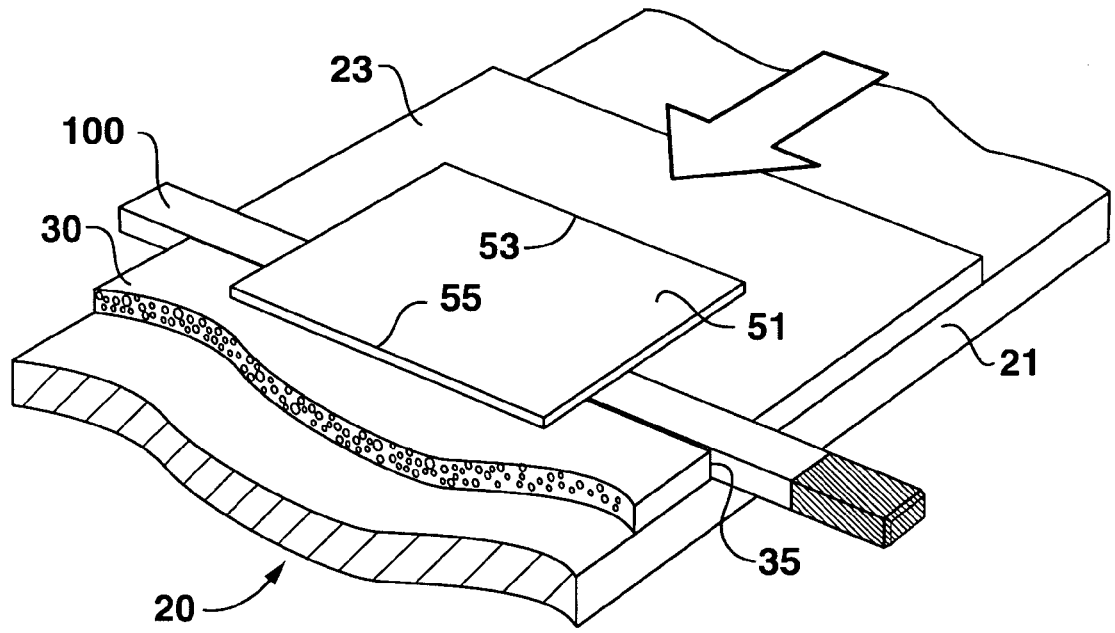
FIG. 4B is a partial perspective view of a portion of the test membrane of FIG. 4A illustrating insertion of the sample meter and use of a bridge member to facilitate diluent and sample flow to a detection region of the membrane.

The channel 35 may be defined completely through the membrane 23 such that continuity of the membrane material is broken at the channel, as depicted in FIGS. 4A and 4B. In this instance, the meter 100 may rest on the support 21 (with backing strip 116 adjacent the support 21). In such an embodiment, a bridge member 51 may be placed over the channel 35 prior to application of a diluent (indicated by the arrow in FIG. 4B) so as to be in fluid communication with the separate membrane components and sample meter 100 to initiate flow of the test sample from the storage section 108 of the membrane 100 to the collection region 30 of the membrane 23. More specifically, the bridging member 51 has a first end 53 that is contiguous and in fluid communication with the membrane 23 at a location nearer to point of diluent application, and a second opposing end 55 that is also contiguous and in fluid communication with the collection region 30 of the membrane 23. The bridging member 51 provides a capillary "lift" that pulls the test sample volume and diluent from the sample meter storage region 108. Once absorbed by the bridging member 51, the test sample is capable of flowing along the bridging member 51 and through the membrane 23 to the collection region 30 of the membrane 23, and further on to the detection zone 31 for analysis. The bridging member 51 may be formed from any material through which the test sample is capable of flowing. For example, the bridging member 51 may be formed from any of the membrane-based materials described above for use in forming the membrane 23. Some specific materials that may be used include, but are not limited to, nylon, nitrocellulose, cellulose, porous polyethylene pads, and glass fiber filter paper.

In addition to the separation membrane 112, it may be desired to provide the bridge member 51, or channel 35, with a blood separation functionality to ensure essentially complete separation of the blood cell components from the test sample. In this regard, the bridge member 51 or channel 35 may incorporate a blood separation material or substance, such as a red blood cell agglutinating reagent (e.g., agglutinin). Agglutinin may be a lectin, such as concanavalin A or *Lycopersicon esculentum*, or an antibody that specifically binds erythrocytes, such as a polyclonal rabbit anti-human erythrocyte antibody preparation. Agglutinins are typically applied in an amount sufficient to agglutinate most of the erythrocytes in the test sample. Other reagents may also be applied to selectively bind or retard movement of certain other biological sample constituents. For example, the bridge member 51 or channel 35 may be treated with a reagent that separates red blood cells from plasma so that plasma components, such as an analyte (e.g., C-reactive protein), may be analyzed. Alternatively, a reagent may be applied that selectively separates biological sample components by their biological, chemical, or physical properties. Other reagents that reduce non-specific binding or non-specific adsorption of components of the blood sample may be used to treat the channel 35 or bridge member 51, including a protein, such as albumin (e.g., bovine serum albumin).

Figure 5A:
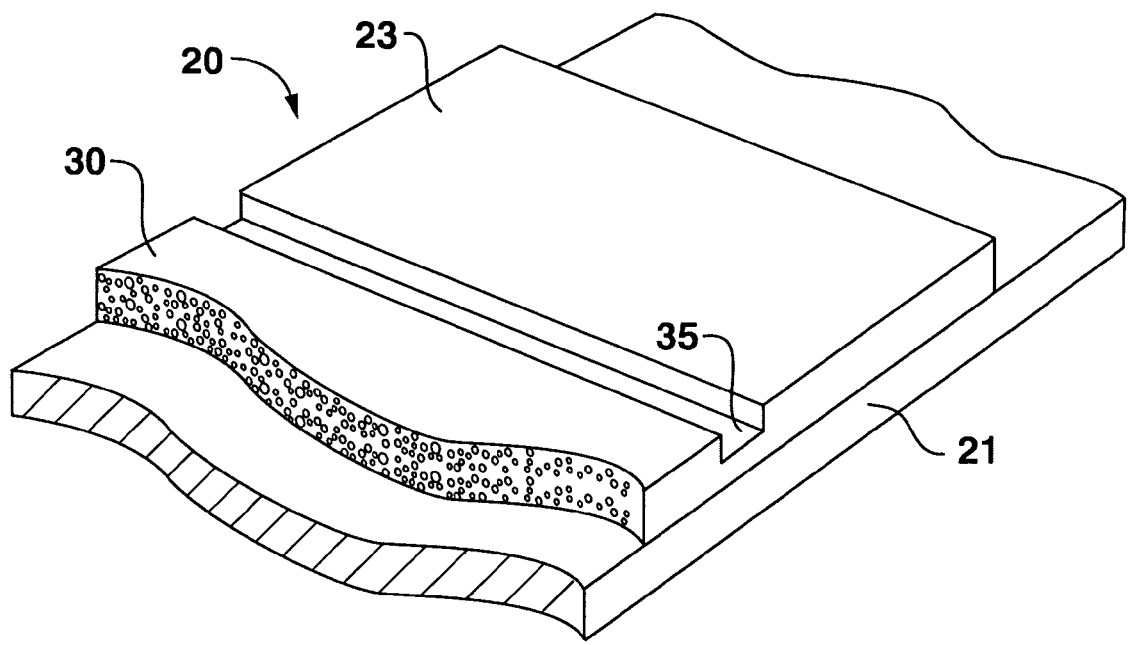
FIG. 5A is a perspective view of an embodiment of a test membrane configured for use with a sample meter within a lateral flow assay device.
Figure 5B:
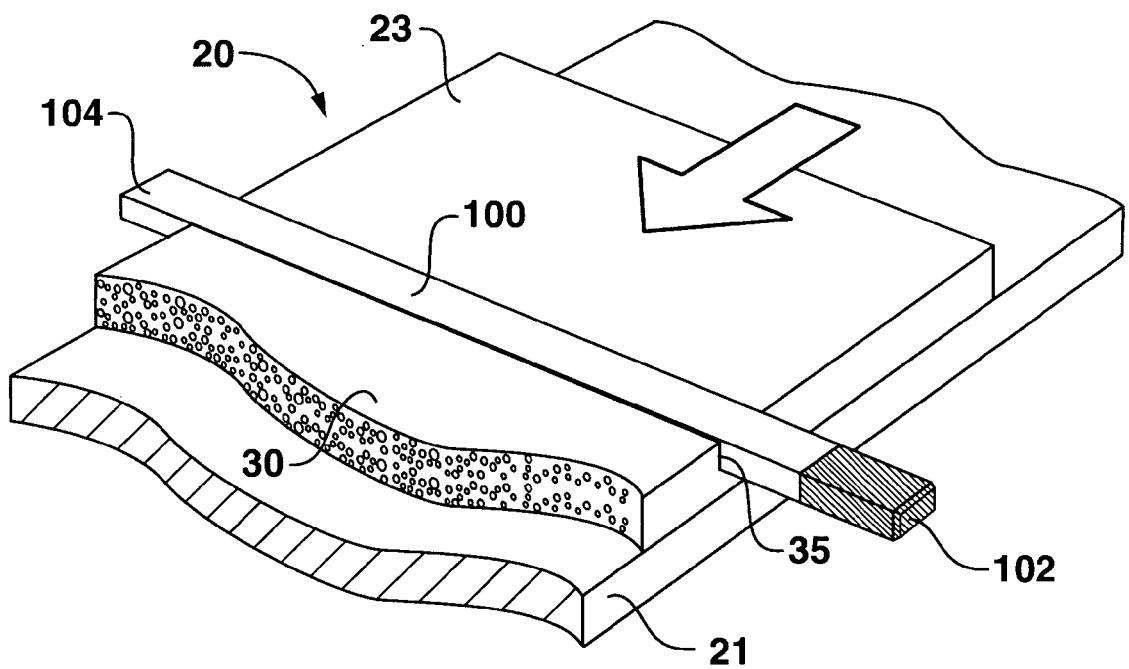
FIG. 5B is a partial perspective view of a portion of the test membrane of FIG. 5A illustrating insertion of the sample meter.

FIGS. 5A and 5B illustrate an embodiment wherein a channel structure 35 is defined in the membrane 23 similar to the channel discussed above with respect to FIGS. 4A and 4B. However, in this embodiment the channel 35 is not defined completely through the membrane material. The meter 100 is placed within channel 35 with the backing strip 116 facing up. Thus, fluid continuity of the membrane material is maintained and a separate member, such as the bridge member 51, may not be necessary to ensure transfer of the sample from the meter 100 to the collection region 30 of the membrane 23. Referring to FIG. 5B, diluent flow may be applied to the upstream region of the membrane 23, as indicated by the arrow, and will flow to the storage section 108 of the membrane 100. So long as the walls and floor structure of the channel 35 remain permeable, the diluent and sample mixture will migrate into the collection region 30 of the membrane 23. It should be appreciated, however, that if the fabrication technique used to define the channel 35 renders the walls and bottom surface of the channel impermeable to the diluent, then a member such as the bridge member 51 may be necessary to facilitate flow of the sample and diluent into the storage region 30. Various fabrication techniques for defining a channel structure 35 within the membrane 23 are described in greater detail below.

Figure 6A:
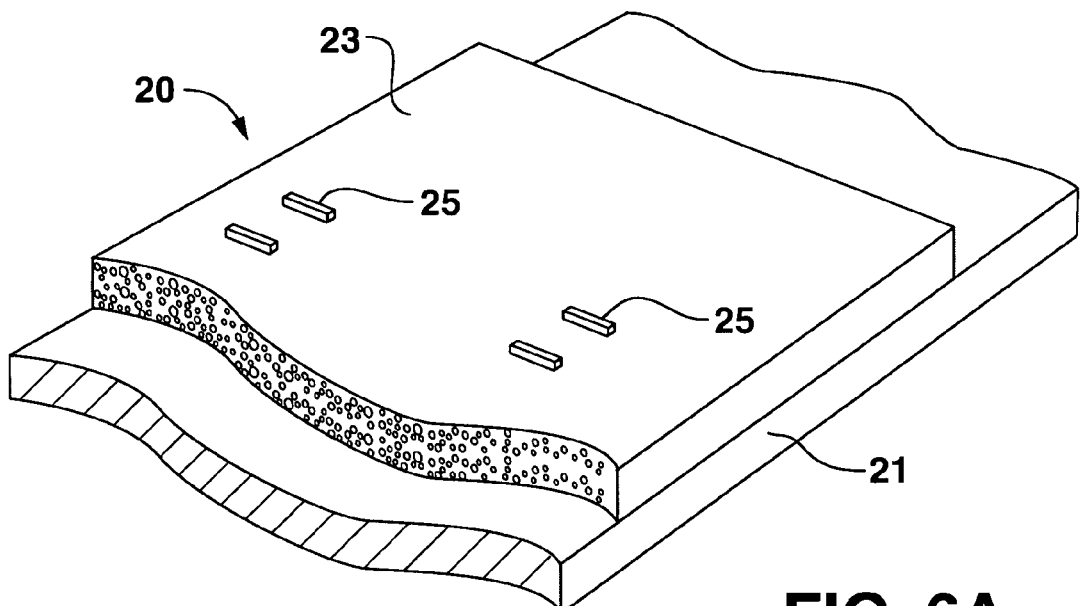
FIG. 6A is a perspective view of an embodiment of a test membrane configured for use with a sample meter within a lateral flow assay device.
Figure 6B:
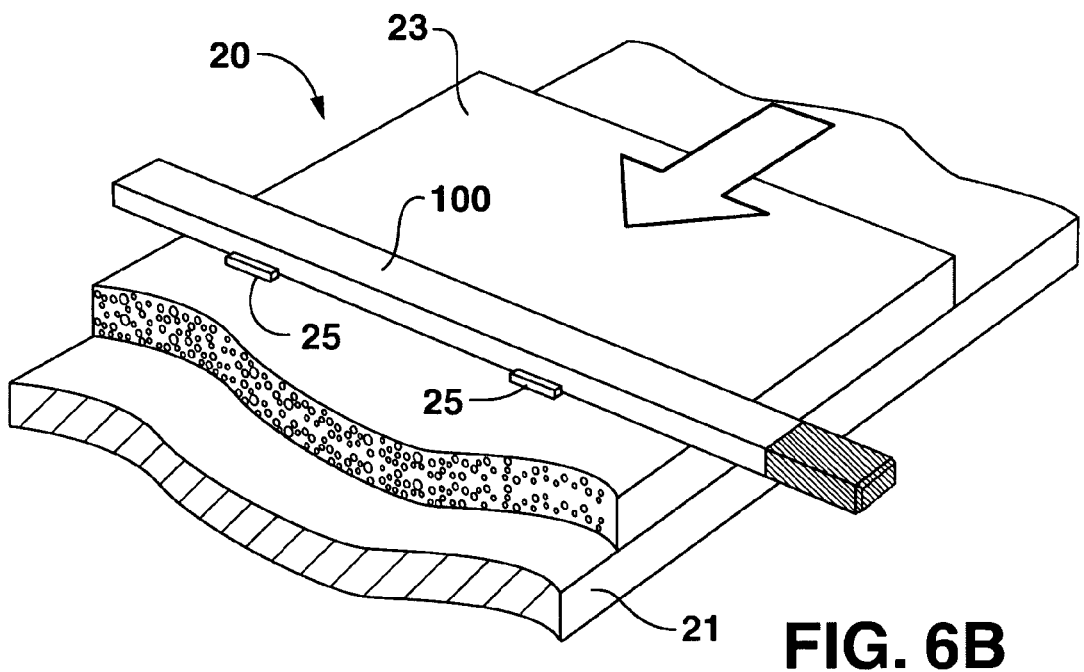
FIG. 6B is a partial perspective view of a portion of the test membrane of FIG. 6A illustrating insertion of the sample meter.

In the embodiment of FIGS. 6A and 6B, the assay device includes guide structure 25 that serves to align the sample meter 100 on the top surface of the membrane 23. This guide structure 25 may simply be raised members on the top surface of the membrane 23, or disposed on the upper housing member 18. Any suitable arrangement and disposition of guide structure may be utilized to define a resting position for the sample meter 100 on the membrane 23 across the path of diluent flow in the membrane, as indicated by the arrow in FIG. 6B.

The ability of the various channel structures 35 to take up an aqueous sample (e.g., serum or plasma and diluent) by capillary action is improved when surface tension of the channel surfaces is near or exceeds the surface tension of water (i.e., 72 mN/m). Thus, if desired, the channel 35 may be treated with one or more wetting agents to increase surface tension. One type of wetting agent that may be used in the present invention is a hydrophilic wetting agent, such as a nonionic surfactant. Examples of suitable nonionic surfactants include ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa.; the TWEEN® range of polyoxyethylene surfactants available from Fisher Scientific of Pittsburgh, Pa.; and the TRITON® range of polyoxyethylene surfactants (e.g., TRITO N® X-100, polyoxyethylene-10 isooctylcyclohexyl ether) available from Sigma-Aldrich Chemical Co. of St. Louis, Mo.

Besides surfactants, still other suitable wetting agents may include water-soluble or water-swellable polymers that are substantially more lubricious when wetted with water, or with a water or alcohol-based electrolyte, than when dry. Examples of such hydrophilic polymers include, for instance, sodium, potassium and calcium alginates, carboxymethylcellulose, agar, gelatin, polyvinyl alcohol, collagen, pectin, chitin, chitosan, poly($\alpha$-amino acids), polyester, poly-1-caprolactone, polyvinylpyrrolidone, polyethylene oxide, polyvinyl alcohol, polyether, polysaccharide, hydrophilic polyurethane, polyhydroxyacrylate, polymethacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, acrylic acid, and combinations thereof.

The channel 35 may generally be formed using any of a variety of different techniques. For example, the channel 35 may be formed by simply laminating separate portions of a membrane onto a support material 21 so that a channel is formed therebetween. As a result, the walls of the metering channel 35 are at least partially formed by respective membrane structures and will be conductive to the diluent and sample across the width of the channel and into the collection region 30 of the membrane 23.

The channel 35 may be microfabricated into the membrane 23. Such a microfabrication technique employs only a confined region of the membrane material for channel formation without adversely affecting the remaining portions. Various mechanical microfabrication techniques may be used to accomplish such channel formation, and include, for instance, cutting, laser ablation, photolithography, and so forth. For example, in one particular embodiment of the present invention, laser ablation techniques are used to form the metering channel 35. Laser ablation generally refers to a process for removing a material using incident light of a certain wavelength. In polymeric materials, for instance, the incident light generally induces photochemical changes in the polymer that results in chemical dissolution. Any known laser may be employed in the present invention, including, for instance, $CO_2$, pulsed light lasers, diode lasers, ND Yag 1064 nm & 532 nm lasers, Alexandrite and Q-switched lasers, pulsed dye lasers, optical and RF lasers, erbium lasers, ruby lasers, and holmium lasers. For example, a $CO_2$ laser may be used to etch a nitrocellulose membrane that is mounted on a supporting fixture. Through use of a moving beam or an X-Y table, precision channels may be generated on the nitrocellulose. In addition, various other known optical devices may be employed in conjunction with the laser to enhance the channel formation, such as optical lenses, mirrors, etc. The parameters of the laser ablation technique, such as wavelength, pulse duration, pulse repetition rate, and beam quality, may be selected for forming the channel 35 as is well known to those skilled in the art.

Chemical microfabrication techniques may also be employed in the present invention to form the channel 35. For example, a solvent treatment may be employed in the present invention that exhibits a dissolving capacity for the membrane 23. To ensure that dissolution of the membrane 23 remains confined within the regions of the channel 35, the dissolving capacity (solvency) of the solvent treatment is generally optimized so that it may quickly form the channel 35 before flowing to other regions of the membrane 23. Some examples of suitable solvents that may be used in the solvent treatment include glycols, such as propylene glycol, butylene glycol, triethylene glycol, hexylene glycol, polyethylene glycols, ethoxydiglycol, and dipropyleneglycol; glycol ethers, such as methyl glycol ether, ethyl glycol ether, and isopropyl glycol ether; ethers, such as diethyl ether and tetrahydrofuran; alcohols, such as methanol, ethanol, n-propanol, iso-propanol, and butanol; triglycerides; ketones, such as acetone, methyl ethyl ketone, and methyl isobutyl ketone; esters, such as ethyl acetate, butyl acetate, and methoxypropyl acetate; amides, such as dimethylformamide, dimethylacetamide, dimethylcaprylic/capric fatty acid amide and N-alkylpyrrolidones; nitriles, such as acetonitrile, propionitrile, butyronitrile and benzonitrile; sulfoxides and sulfones, such as dimethyl sulfoxide (DMSO) and sulfolane; and so forth.

Of course, the selected solvent will vary depending on the material used to form the membrane 23. In one particular embodiment, for example, the membrane 23 is formed from nitrocellulose. Examples of solvents that are capable of dissolving nitrocellulose (i.e., active solvents) include ketones, such as acetone, methyl ethyl ketone, and methyl isobutyl ketone; esters, such as ethyl acetate, butyl acetate, and methoxy propyl acetate; glycol ethers, such as methyl glycol ether, ethyl glycol ether, and isopropyl glycol ether; and alcohols, such as methanol and ethanol. In some embodiments, a latent solvent may be employed that is only capable of dissolving nitrocellulose under certain conditions, such as at a higher temperature or in the presence of an active solvent. Examples of such latent solvents may include, for instance, ethanol, isopropanol, and butanol. In some cases, a mixture of an active solvent and a co-solvent (e.g., latent solvent or other active solvent) may be employed. Such co-solvents may provide synergistic improvement to the dissolving capacity of the active solvent, or may simply be employed to reduce costs. When utilized, the active solvent is typically present in an amount greater than about 50 vol. %, in some embodiments greater than about 60 vol. %, and in some embodiments, from about 70 vol. % to about 95 vol. %. Likewise, the co-solvent may be present in an amount less than about 50 vol. %, in some embodiments less than about 40 wt. %, and in some embodiments, from about 5 vol. % to about 30 vol. %. In still other embodiments, a mixture of two or more latent solvents may be employed.

The purity of a solvent may also influence its dissolving capacity. That is, higher solvent purities generally result in a higher dissolving capacity. Thus, to optimize dissolving capacity, it is normally desired that the purity of the solvent likewise be optimized. For example, in most embodiments, the purity of a solvent employed in the present invention is greater than about 95 mass %, in some embodiments greater than about 98 mass %, and in some embodiments, greater than about 99 mass %.

The solvent treatment may be applied to the membrane using any of a variety of well-known application techniques. Suitable application techniques include, for example, spraying, printing (e.g., inkjet, pad, etc.), pipette, air brushing, metering with a dispensing pump, and so forth. In one particular embodiment, for example, the solvent treatment is applied using a dispensing and optional drying process commonly employed to form detection lines on lateral flow strips. Such a system could involve placing a sheet of the porous membrane on a dispensing machine and threading it through a rewind spindle. This may be accomplished using either a batch or continuous process. The dispensing machine delivers a precise volume of the solvent treatment in a straight line as the membrane passes beneath. The sheet then passes through a drier and is wound back on a spool for further processing. One such lab-scale dispensing pump system for batch processes is available from Kinematic Automation, Inc. of Twain Harte, Calif. under the name "Matrix™ 1600."

The solvent treatment may also be applied in any amount effective to form the channel 35 with the desired size and shape. The ultimate amount employed may depend on a variety of factors, including the dissolving capacity of the solvent for the membrane 23, the speed of application, etc. For example, in some embodiments, the solvent treatment is applied in an amount of from about 0.01 to about 10 microliters per centimeter in width of the membrane, in some embodiments from about 0.1 to about 10 microliters per centimeter in width of the membrane, and in some embodiments, from about 0.5 to about 5 microliters per centimeter in width of the membrane 23.

Regardless of the particular mechanism or method used to position the sample meter 100 relative to the membrane 23, a diluent (or washing agent) is generally employed to upstream to facilitate delivery of the test sample from the storage section 108 of the meter 100 to the collection region 30 of the membrane 23.

The diluent may be any material having a viscosity that is sufficiently low to allow movement of the fluid by capillary action and that supports a reaction between the analyte and any binding agents (e.g., does not interfere with antibody/antigen interaction). In one embodiment, the diluent contains water, a buffering agent; a salt (e.g., NaCl); a protein stabilizer (e.g., BSA, casein, trehalose, or serum); and/or a detergent (e.g., nonionic surfactant). Representative buffering agents include, for example, phosphate-buffered saline (PBS) (e.g., pH of 7.2), 2-(N-morpholino) ethane sulfonic acid (MES) (e.g., pH of 5.3), HEPES buffer, TBS buffer, etc., and so forth.

Test kits 20 in accordance with the invention may incorporate an internal source of diluent that is applied so as to flow to the collection region subsequent to insertion of the sample meter 100 into the assay housing 15. For example, referring to FIG. 7, an internal diluent source 118 is illustrated as a pouch or container 120 having the diluent contained therein. Means 134 are provided for rupturing or otherwise breaching the pouch 120 subsequent to insertion of the sample meter 100 into the housing 15. For example, in the embodiment illustrated in FIG. 7, the means 134 includes a push button mechanism 138 or other manually actuated device that is readily configured with the assay housing 15. Upon actuation of the member 138, points 136 or a blade configured on the bottom of the mechanism 138 pierces the pouch 120 causing the diluent to flow towards the collection region of the membrane 23. Sustained depression of the finger actuated member 138 may also serve to compress the pouch 120 and force the diluent therefrom in the direction of the collection region 30 of the membrane 23.

It should be appreciated that any number of manually actuated devices may be readily configured by those skilled in the art for the purpose of rupturing an internal source of diluent within the assay housing 15, and all such devices are within the scope and spirit of the invention.

Figure 8:
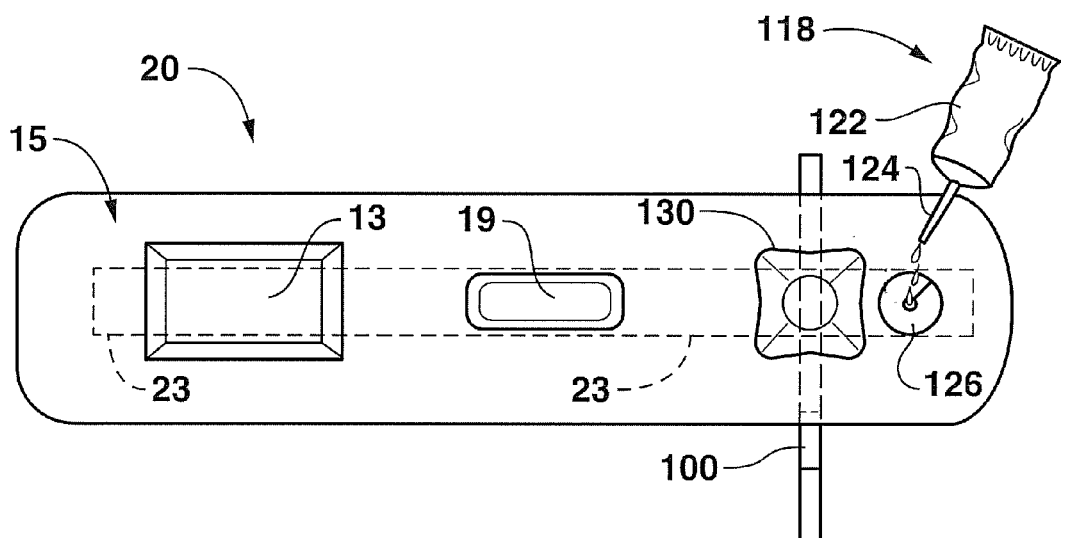
FIG. 8 is a top view of an embodiment of a lateral flow assay device configured for receipt of a diluent from an external source.

In an alternate embodiment illustrated, for example in FIG. 8, the test kit 20 may include an external diluent source 118. In the illustrated embodiment, this external source is illustrated as a capsule 122 or other disposable container, preferably a squeezable container having a nozzle 124 configured for insertion into a port 126 defined in the assay housing 15. The port 126 is disposed so that the diluent is supplied upstream of the sample meter 100 and cause to flow towards the collection region of the membrane 23. Internal diluent directing structure, such as channels or the like, may be defined within the housing 15 to more precisely direct the diluent to the desired location.

Figure 7:
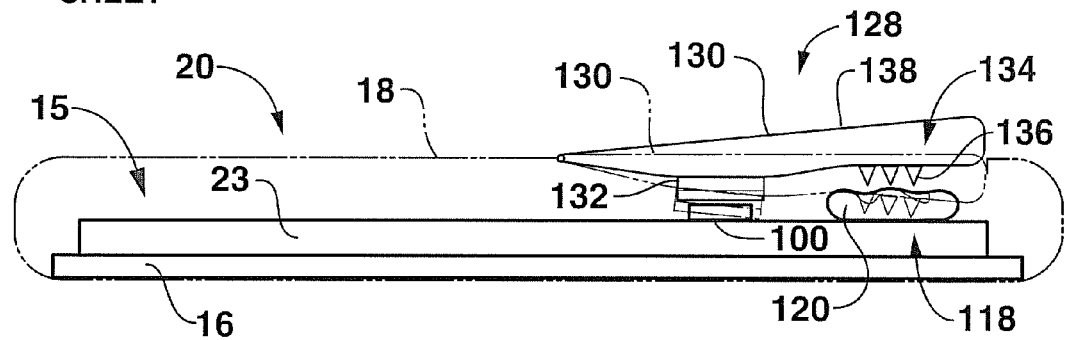
FIG. 7 is cross-sectional view of a later flow assay device incorporating a mechanism to score or cut the test membrane and to rupture an internal container of diluent.

In certain applications, it may be desired to present a precisely defined portion of the storage section 108 of the sample meter 100 to the collection region of the membrane 23 by cutting or scoring the meter 100. In this regard, means 128 may be provided for cutting or scoring the meter 100 subsequent to insertion of the meter into the housing 15 and in conjunction with, or before, supplying the diluent. The means 128 may take on various forms. For example, in the embodiment illustrated in FIGS. 7 and 8, the means 128 include a manually actuated device 130, such as a push button device, that is configured with the assay housing 15 with a blade 132 or knife edge disposed so as to cut or score the sample meter 100 upon actuation of the member 130 by the user. As depicted in FIG. 7, this manually actuated device 130 may be incorporated with the same manual device 138 used to breach or rupture an internal diluent pouch 120, as discussed above. In the embodiment of FIG. 8, a dedicated finger actuated member 130 is provided for the purpose of cutting or scoring the membrane 100. The finger actuated member 130 may also serve as a device for pressing the member 100 into contact with the membrane 23. For example, instructions may be provided to the user to depress the member 130 and hold the member in this depressed condition for a sufficient period of time to ensure that the sample meter 100 is pressed into fluid communication with the membrane 23 as the diluent is supplied upstream of the meter 100.

In addition to the components set forth above, the diagnostic test kit of the present invention may also contain various other components to enhance detection accuracy. For exemplary purposes only, one embodiment of an immunoassay that may be performed in accordance with the present invention to detect the presence will now be described in more detail. Immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a biological sample.

To facilitate the detection of the analyte within the test sample, a substance may be pre-applied to the sample meter 100, or previously mixed with the diluent or test sample, which is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. Nos. 5,670,381 to Jou, et al. and 5,252, 459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. Nos. 6,261,779 to Barbera-Guillem, et al. and 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. Nos. 4,614,723 to Schmidt, et al.; 5,464,741 to Hendrix; 5,518,883 to Soini; 5,922,537 to Ewart, et al.; 6,004,530 to Sagner. et al.; and 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are note limited to, bis[(4,4'-carbomethoxy)-2,2'-bipyridine] 2-[3-(4-methyl-2,2'-bipyridine-4-yl)propyl]-1,3-dioxolane ruthenium (II); bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid] ruthenium (II); tris(2,2'bipyridine) ruthenium (II); (2,2'-bipyridine) [bis-bis(1,2-diphenylphosphino)ethylene] 2-[3-(4-methyl-2,2'-bipyridine-4'-yl) propyl]-1,3-dioxolane osmium (II); bis(2,2'-bipyridine)[4-(4'-methyl-2,2'-bipyridine)-butylamine]ruthenium (II); bis (2,2'-bipyridine)[1-bromo-4(4'-methyl-2,2'-bipyridine-4-yl) butane]ruthenium (II); bis(2,2'-bipyridine) maleimidohexanoic acid, 4-methyl-2,2'-bipyridine-4'-butylamide ruthenium (II), and so forth. Still other suitable metal complexes that may exhibit phosphorescent properties may be described in U.S. Pat. Nos. 6,613,583 to Richter, et al.; 6,468,741 to Massey, et al.; 6,444,423 to Meade, et al.; 6,362, 011 to Massey, et al.; 5,731,147 to Bard, et al.; and 5,591,581 to Massey, et al., which are incorporated herein in their entirety by reference thereto for all purposes.

In some cases, luminescent compounds may have a relatively long emission lifetime may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (III)). Such chelates may exhibit strongly redshifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. Nos. 6,030,840 to Mullinax, et al.; 5,585,279 to Davidson; 5,573,909 to Singer, et al.; 6,242,268 to Wieder, et al.; and 5,637,509 to Hemmila, et al., which are incorporated herein in their entirety by reference thereto for all purposes.

Detectable substances, such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. Nos. 5,670,381 to Jou, et al.; 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometer to about 100 microns, some embodiments, from about 1 nanometer to about 10 microns, and in some ebodiments, from about 10 about 100 nanometers.

In some instances, it may be desired to modify the detecton probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, anibodies (primary or secondary), and complexes thereof, including those formed by recombinant DNA methods or peptide synthesis. An antibody may be monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin an avidin (or derivatives thereof), biotin and streptavidin, carbohydrates and lectins, complementary nucleotide sequences (including probe and capture nucleic acid sequences used in DNA hybridization assays to detect a target nucleic acid sequence), complemntary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte (i.e., "analog") may be used so long as it has at least one epitope in common with the analyte.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, such as with poly(thiophenol), the detection probes may be capable of direct covalent linking with a protein without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

Referring again to the figures in general, after passing through the collection region 30, the diluent and test sample travel through the membrane 23 until reaching the detection zone 31. Upon reaching the detection zone 31, the volume of the test sample is relatively uniform across the entire width of the detection zone 31. In addition, as a result of the known saturation volume of the collection region 30, the volume of the test sample is also predetermined within a narrow range.

Within the detection zone 31, a receptive material is immobilized that is capable of binding to the conjugated detection probes. The receptive material may be selected from the same materials as the specific binding members described above, including, for instance, antigens; haptens; antibody-binding proteins, such as protein A, protein G, or protein A/G; neutravidin (a deglycosylated avidin derivative), avidin (a highly cationic 66,000-dalton glycoprotein), streptavidin (a nonglycosylated 52,800-dalton protein), or captavidin (a nitrated avidin derivative); primary or secondary antibodies, and derivatives or fragments thereof. In one embodiment, for example, the receptive material is an antibody specific to an antigen within the test sample. The receptive material serves as a stationary binding site for complexes formed between the analyte and the conjugated detection probes. Specifically, analytes, such as antibodies, antigens, etc., typically have two or more binding sites (e.g., epitopes). Upon reaching the detection zone 31, one of these binding sites is occupied by the specific binding member of the conjugated probe. However, the free binding site of the analyte may bind to the immobilized first receptive material. Upon being bound to the immobilized receptive material, the complexed probes form a new ternary sandwich complex.

Other than the detection zone 31, the lateral flow device 20 may also define various other zones for enhancing detection accuracy. For example, in embodiments in which high analyte concentrations are a concern, the assay device 20 may contain an indicator zone 33 that is positioned downstream from the detection zone 31 and is configured to provide information as to whether the analyte concentration has reached the saturation concentration ("hook effect" region) for the assay. The indicator zone 33 contains a second receptive material that is immobilized on the membrane 23 and serves as a stationary binding site for the conjugated detection probes. To accomplish the desired binding within the indicator zone 33, it is generally desired that the second receptive material is capable of differentiating between those detection probes that are complexed with the analyte and those that remain uncomplexed. For example, in one embodiment, the second receptive material includes a molecule that has at least one epitope in common with the analyte, such as analyte molecules, or derivatives or fragments (i.e., analog) thereof, so that it is capable of specifically binding to an antibody conjugate when it is uncomplexed with the analyte.

Alternatively, the second receptive material may include a biological material that is not an analyte molecule or analog thereof, but nevertheless is capable of preferentially binding to uncomplexed conjugated detection probes. In one embodiment, for example, the first receptive material may be a monoclonal antibody, such as anti-CRP $IgG_1$. The detection probes are conjugated with a monoclonal antibody different than the monoclonal antibody of the first receptive material, such as anti-CRP $IgG_2$. In this particular embodiment, the second receptive material may be a secondary antibody, such as Goat anti-human, IgG F(ab')$_2$, which has been adsorbed against Fc fragments and therefore reacts only with the $F_{ab}$ portion of IgG. Thus, when no analyte is present, the secondary antibody is able to bind to the free "$F_{ab}$" binding domain of the anti-CRP $IgG_2$ monoclonal antibody. However, when an antigen is present in the test sample, it first complexes with the "$F_{ab}$" binding domain of the anti-CRP $IgG_2$ monoclonal antibody. The presence of the antigen renders the "$F_{ab}$" binding domain unavailable for subsequent binding with the secondary antibody. In this manner, the secondary antibody within the indicator zone 35 is capable of preferentially binding to uncomplexed detection probes.

Although the detection zone 31 and optional indicator zone 33 may provide accurate results, it is sometimes difficult to determine the relative concentration of the analyte within the test sample under actual test conditions. Thus, the assay device 20 may include a calibration zone 32. In this embodiment, the calibration zone 32 is formed on the membrane 23 and is positioned downstream from the detection zone 31 and optional indicator zone 33. Alternatively, however, the calibration zone 32 may also be positioned upstream from the detection zone 31 and/or optional indicator zone 33. The calibration zone 32 is provided with a third receptive material that is capable of binding to any calibration probes that pass through the length of the membrane 23. When utilized, the calibration probes may contain a detectable substance that is the same or different than the detectable substance used for the detection probes. Moreover, the calibration probes may also be conjugated with a specific binding member, such as described above. For example, in one embodiment, biotinylated calibration probes may be used. Generally speaking, the calibration probes are selected in such a manner that they do not bind to the first or second receptive material at the detection zone 31 and indicator zone 33. The third receptive material of the calibration zone 32 may be the same or different than the receptive materials used in the detection zone 31 or indicator zone 33. For example, in one embodiment, the third receptive material is a biological receptive material, such as antigens, haptens, antibody-binding proteins (e.g., protein A, protein G, or protein A/G), neutravidin, avidin, streptavidin, captavidin, primary or secondary antibodies, or complexes thereof. It may also be desired to utilize various non-biological materials for the third receptive material (e.g., polyelectrolytes) of the calibration zone 32, such as described in U.S. patent application Pub. No. 2003/0124739 to Song, et al., which is incorporated herein in its entirety by reference thereto for all purposes.

When utilized, the polyelectrolytes may have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethyleneimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridnium iodide) and poly (styryl-b-acrylic acid), both of which are available from Polymer Source, Inc. of Dorval, Canada.

Although any polyelectrolyte may generally be used, the polyelectrolyte selected for a particular application may vary depending on the nature of the detection probes, the calibration probes, the membrane, and so forth. In particular, the distributed charge of a polyelectrolyte allows it to bind to substances having an opposite charge. Thus, for example, polyelectrolytes having a net positive charge are often better equipped to bind with probes that are negatively charged, while polyelectrolytes that have a net negative charge are often better equipped to bind to probes that are positively charged. Thus, in such instances, the ionic interaction between these molecules allows the required binding to occur within the calibration zone 32. Nevertheless, although ionic interaction is primarily utilized to achieve the desired binding in the calibration zone 32, polyelectrolytes may also bind with probes having a similar charge.

Because the polyelectrolyte is designed to bind to probes, it is typically desired that the polyelectrolyte be substantially non-diffusively immobilized on the surface of the membrane 23. Otherwise, the probes would not be readily detectable by a user. Thus, the polyelectrolytes may be applied to the membrane 23 in such a manner that they do not substantially diffuse into the matrix of the membrane 23. In particular, the polyelectrolytes typically form an ionic and/or covalent bond with functional groups present on the surface of the membrane 23 so that they remain immobilized thereon. Although not required, the formation of covalent bonds between the polyelectrolyte and the membrane 23 may be desired to more permanently immobilize the polyelectrolyte thereon. For example, in one embodiment, the monomers used to form the polyelectrolyte are first formed into a solution and then applied directly to the membrane 23. Various solvents (e.g., organic solvents, water, etc.) may be utilized to form the solution. Once applied, the polymerization of the monomers is initiated using heat, electron beam radiation, free radical polymerization, and so forth. In some instances, as the monomers polymerize, they form covalent bonds with certain functional groups of the membrane 23, thereby immobilizing the resulting polyelectrolyte thereon. For example, in one embodiment, an ethyleneimine monomer may form a covalent bond with a carboxyl group present on the surface of some membranes (e.g., nitrocellulose).

In another embodiment, the polyelectrolyte may be formed prior to application to the membrane 23. If desired, the polyelectrolyte may first be formed into a solution using organic solvents, water, and so forth. Thereafter, the polyelectrolytic solution is applied directly to the membrane 23 and then dried. Upon drying, the polyelectrolyte may form an ionic bond with certain functional groups present on the surface of the membrane 23 that have a charge opposite to the polyelectrolyte. For example, in one embodiment, positively-charged polyethyleneimine may form an ionic bond with negatively-charged carboxyl groups present on the surface of some membranes (e.g., nitrocellulose).

In addition, the polyelectrolyte may also be crosslinked to the membrane 23 using various well-known techniques. For example, in some embodiments, epichlorohydrin-functionalized polyamines and/or polyamidoamines may be used as a crosslinkable, positively-charged polyelectrolyte. Examples of these materials are described in U.S. Pat. Nos. 3,700,623 to Keim and 3,772,076 to Keim, 4,537,657 to Keim, which are incorporated herein in their entirety by reference thereto for all purposes and are believed to be sold by Hercules, Inc., Wilmington, Del. under the Kymene™ trade designation. For instance, Kymene™ 450 and 2064 are epichlorohydrin-functionalized polyamine and/or polyamidoamine compounds that contain epoxide rings and quaternary ammonium groups that may form covalent bonds with carboxyl groups present on certain types of membranes (e.g., nitrocellulose) and crosslink with the polymer backbone of the membrane when cured. In some embodiments, the crosslinking temperature may range from about 50° C. to about 120° C. and the crosslinking time may range from about 10 to about 600 seconds.

Although various techniques for non-diffusively immobilizing polyelectrolytes on the membrane 23 have been described above, it should be understood that any other technique for non-diffusively immobilizing polyelectrolytic compounds may be used in the present invention. In fact, the aforementioned methods are only intended to be exemplary of the techniques that may be used in the present invention. For example, in some embodiments, certain components may be added to the polyelectrolyte solution that may substantially inhibit the diffusion of such polyelectrolytes into the matrix of the membrane 23.

The detection zone 31, indicator zone 33, and calibration zone 32 may each provide any number of distinct detection regions so that a user may better determine the concentration of one or more analytes within a test sample. Each region may contain the same receptive materials, or may contain different receptive materials. For example, the zones may include two or more distinct regions (e.g., lines, dots, etc.). The regions may be disposed in the form of lines in a direction that is substantially perpendicular to the flow of the test sample through the assay device 20. Likewise, in some embodiments, the regions may be disposed in the form of lines in a direction that is substantially parallel to the flow of the test sample through the assay device 20.

In some cases, the membrane 23 may also define a control zone (not shown) that gives a signal to the user that the assay is performing properly. For instance, the control zone (not shown) may contain an immobilized receptive material that is generally capable of forming a chemical and/or physical bond with probes or with the receptive material immobilized on the probes. Some examples of such receptive materials include, but are not limited to, antigens, haptens, antibodies, protein A or G, avidin, streptavidin, secondary antibodies, and complexes thereof. In addition, it may also be desired to utilize various non-biological materials for the control zone receptive material. For instance, in some embodiments, the control zone receptive material may also include a polyelectrolyte, such as described above, that may bind to uncaptured probes. Because the receptive material at the control zone is only specific for probes, a signal forms regardless of whether the analyte is present. The control zone may be positioned at any location along the membrane 23, but is preferably positioned downstream from the detection zone 31 and the indicator zone 33.

Qualitative, semi-quantitative, and quantitative results may be obtained in accordance with the present invention. For example, when it is desired to semi-quantitatively or quantitatively detect an analyte, the intensity of any signals produced at the detection zone 31, indicator zone 33, and/or calibration zone 32 may be measured with an optical reader. The actual configuration and structure of the optical reader may generally vary as is readily understood by those skilled in the art. For example, optical detection techniques that may be utilized include, but are not limited to, luminescence (e.g., fluorescence, phosphorescence, etc.), absorbance (e.g., fluorescent or non-fluorescent), diffraction, etc. One suitable reflectance spectrophotometer is described, for instance, in U.S. Patent App. Pub. No. 2003/0119202 to Kaylor, et al., which is incorporated herein in its entirety by reference thereto for all purposes. In another embodiment, a reflectance-mode spectrofluorometer may be used to detect the intensity of a fluorescence signal. Suitable spectrofluorometers and related detection techniques are described, for instance, in U.S. Patent App. Pub. No. 2004/0043502 to Song, et al., which is incorporated herein in its entirety by reference thereto for all purposes. Likewise, a transmission-mode detection system may also be used to signal intensity.

Although various embodiments of device configurations have been described above, it should be understood, that a device of the present invention may generally have any configuration desired, and need not contain all of the components described above. Various other device configurations, for instance, are described in U.S. Pat. Nos. 5,395,754 to Lambotte, et al.; 5,670,381 to Jou, et al.; and 6,194,220 to Malick, et al., which are incorporated herein in their entirety by reference thereto for all purposes.

Various assay formats may also be used to test for the presence or absence of an analyte using the assay device of the present invention. For instance, a "sandwich" format typically involves mixing the test sample with detection probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described by U.S. Pat. Nos. 4,168,146 to Grubb, et al. and 4,366,241 to Tom, et al., which are incorporated herein in their entirety by reference thereto for all purposes. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. Nos. 4,235,601 to Deutsch, et al., 4,442,204 to Liotta, and 5,208,535 to Buechler, et al., which are incorporated herein in their entirety by reference thereto for all purposes. Various other device configurations and/or assay formats are also described in U.S. Pat. Nos. 5,395,754 to Lambotte, et al.; 5,670,381 to Jou, et al.; and 6,194,220 to Malick, et al., which are incorporated herein in their entirety by reference thereto for all purposes.

As a result of the present invention, a controlled volume of a test sample may be uniformly delivered to a detection zone of a lateral flow assay device. Such control over sample flow provides a significant improvement in detection accuracy and sensitivity for lateral flow systems. One particular benefit is that sample application and testing may be done in a relatively quick, easy, and simple manner. Further, as a result of the controlled flow provided by the present invention, low volume test samples may be accurately tested without the requirement of complex and expensive equipment to obtain a useable sample. For example, whole blood drops having a volume of about 5 microliters or less may be readily analyzed for the presence of an analyte in accordance with the present invention.

The present invention may be better understood with reference to the following examples:

EXAMPLES

The ability to form sample meter strips in accordance with the invention was demonstrated as follows:

Assembly

1. A strip (2.5 cm wide by 30 cm length) of nitrocellulose membrane (HF 75 and HF 120 from Millipore Inc.) was hand laminated onto a transparent backed lateral flow card.
2. A 9 mm long piece of separation membrane material (BTS SP 300 from Pall, Inc.) was cut. The other dimension of this piece is dependent on the number of samples desired. For example, for 1 mm wide samples (e.g., 9 mm×1 mm after slitting), then the other dimension would=1 mm×number of samples desired.
3. The BTS 300 membrane was hand laminated (ensure correct side is up) onto the transparent lateral flow card (in the location usually reserved for the gold conjugate) with about a 1 mm overlap between the BTS and nitrocellulose membranes.
4. The opaque paper on the back of the transparent card was removed to ensure that complete slitting of the devices occurs.
5. Using the Kinematic 2360 slitter from Kinematic Automation, Inc., the assembled card was slit to desired dimensions (i.e. 1 mm or 2 mm widths).
6. The Sampling/Metering devices were placed in a plastic storage bag prior to use.

Sampling

1. A 5 microliter (5 ul) sample of blood was placed onto wax paper.
2. The end of the sampling/metering device with the BTS 300 membrane was brought into contact with the blood sample.
3. Blood flow up the sampling and metering device was observed. As the blood reached the nitrocellulose membrane, the membrane became wet as a result of plasma migration along the membrane.
4. Plasma migration along the nitrocellulose membrane for the Millipore HF 75 and HF 120 materials at 1 and 3 minutes after contact with the blood sample is indicated in the below tables:

Evaluating Plasma Yield Using HF75 with BTS 1 mm×9 mm

|  | Time (Minutes) | |  |
| --- | --- | --- | --- |
|  | 1 | 3 |  |
| Blood Sample A | 9.0 mm | 15.5 mm | Trial 1 |
| (Hematocrit 38) | 9.0 mm | 15.0 mm | Trial 2 |
| Blood Sample B | 9.0 mm | 14.0 mm | Trial 1 |
| (Hematocrit 45) | 9.0 mm | 12.5 mm | Trial 2 |
| Blood Sample C | 8.5 mm | 10.0 mm | Trial 1 |
| (Hematocrit 49) | 9.0 mm | 11.0 mm | Trial 2 |

Evaluating Plasma Yield Using HF120 with BTS 1 mm×9 mm

|  | Time (Minutes) | |  |
| --- | --- | --- | --- |
|  | 1 | 3 |  |
| Blood Sample A | 7.5 mm | 11.0 mm | Trial 1 |
| (Hematocrit 38) | 7.0 mm | 11.0 mm | Trial 2 |
| Blood Sample B | 6.5 mm | 9.0 mm | Trial 1 |
| (Hematocrit 45) | 6.0 mm | 8.5 mm | Trial 2 |
| Blood Sample C | 4.0 mm | 4.5 mm | Trial 1 |
| (Hematocrit 49) | 4.0 mm | 4.5 mm | Trial 2 |

While the invention has been described in detail with respect to the specific embodiments thereof, it will be appreciated that those skilled in the art, upon attaining an understanding of the foregoing, may readily conceive of alterations to, variations of, and equivalents to these embodiments.

Accordingly, the scope of the present invention should be assessed as that of the appended claims and any equivalents thereto.

What is claimed is:

1. A diagnostic test kit for detecting the presence of an analyte within a blood test sample, the test kit comprising a lateral flow assay device that further includes:
   a housing, and a membrane disposed within said housing comprising a detection region and a collection region;
   a blood sample meter separate from said housing and removably insertable into said housing, said blood sample meter comprising a first end for absorption of a blood sample, a filtering section adjacent said first end that filters red blood cell components from said blood sample, and a storage section adjacent said filtering section that receives plasma or serum from said filtering section;
   an opening in said housing sized for insertion of said sample meter into said housing such that said storage section of said sample meter is disposed in fluid communication with said collection region of said membrane, wherein said meter is not inserted into said housing until after said meter has been used for absorption, filtering, and storage of the blood sample; and
   wherein, said plasma or serum is transferable from said storage section of said sample meter to said collection region of said membrane for subsequent migration to said detection region; and
   means for cutting or scoring said sample meter along said storage section so as to present a desired length of said storage section to said collection region of said membrane.

2. The test kit of claim 1, further comprising a plurality of detection probes within said detection region that are capable of producing a detectable signal.

3. The test kit of claim 2, wherein a receptive material is immobilized within said detection region that is capable of binding to said detection probes or conjugates thereof.

4. The test kit of claim 1, wherein said sample meter comprises a separation membrane attached to a storage membrane with an overlap between said separation and storage membranes in said filtering section.

5. The test kit of claim 4, wherein said separation membrane has a length of between about 3 to about 12 mm, and said overlap with said storage membrane is between about 1 mm to about 3 mm, said storage membrane having a length of between about 10 mm to about 40 mm.

6. The test kit of claim 4, wherein said separation membrane extends to said first end of said sample meter, and said storage membrane extends to an opposite second end of said sample meter.

7. The test kit of claim 4, wherein said separation and storage membranes are attached to a backing strip.

8. The test kit of claim 7, wherein said backing strip is sufficiently transparent to view plasma or serum in said storage section through said backing strip.

9. The test kit of claim 1, wherein said sample meter is an elongated member having a width of between about 1 mm to about 5 mm, and a length of between about 20 mm to about 40 mm.

10. The test kit of claim 1, further comprising a source of diluent, said diluent applied to said collection region subsequent to insertion of said sample meter into said housing.

11. The test kit of claim 10, wherein said diluent is stored in a rupturable container within said housing, and further comprising means for rupturing said container subsequent to insertion of said sample meter into said housing.

12. The test kit of claim 10, wherein said diluent is supplied from a source external to said housing, said housing further comprising a port for communication with said external diluent source.

13. The test kit of claim 1, wherein said cutting or scoring means comprises a finger actuated member configured with said housing with blades positioned to cut or score said sample member upon actuation of said finger actuated member.

* * * * *